United States Patent
Hwang et al.

(10) Patent No.: US 12,209,967 B2
(45) Date of Patent: *Jan. 28, 2025

(54) APPARATUS FOR MONITORING BIOAEROSOLS AND METHOD THEREOF

(71) Applicant: INDUSTRY-ACADEMIC COOPERATION FOUNDATION, YONSEI UNIVERSITY, Seoul (KR)

(72) Inventors: Jung Ho Hwang, Seoul (KR); Hyeong Rae Kim, Seoul (KR); Sang Gwon An, Uijeongbu-si (KR)

(73) Assignee: INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 756 days.

This patent is subject to a terminal disclaimer.

(21) Appl. No.: 17/181,091

(22) Filed: Feb. 22, 2021

(65) Prior Publication Data

US 2022/0266240 A1 Aug. 25, 2022

(51) Int. Cl.
| | | |
|---|---|---|
| G01N 21/77 | (2006.01) | |
| B01L 3/00 | (2006.01) | |
| C12Q 1/04 | (2006.01) | |
| G01N 1/31 | (2006.01) | |
| G01N 15/14 | (2024.01) | |
| G01N 21/64 | (2006.01) | |
| G01N 21/78 | (2006.01) | |

(52) U.S. Cl.
CPC .............. *G01N 21/77* (2013.01); *B01L 3/502* (2013.01); *B01L 3/52* (2013.01); *C12Q 1/04* (2013.01); *G01N 1/31* (2013.01); *G01N 21/6428* (2013.01); *G01N 21/6458* (2013.01); *B01L 2200/026* (2013.01); *B01L 2200/0647* (2013.01); *B01L 2300/0848* (2013.01); *B01L 2400/0415* (2013.01); *G01N 2015/1481* (2013.01); *G01N 2021/6439* (2013.01); *G01N 21/783* (2013.01)

(58) Field of Classification Search
CPC ...... B01L 3/502; B01L 3/52; B01L 2200/026; B01L 2200/0647; B01L 2300/0848; B01L 2400/0415; B01L 2300/165; B01L 2400/086; B01L 3/50273; B01L 3/502761; C12Q 1/04; G01N 1/31; G01N 21/6428; G01N 21/6458; G01N 21/783; G01N 2021/6439; G01N 15/147; G01N 2001/317; G01N 2015/0046; G01N 2015/0065; G01N 2015/1481; G01N 2015/1488; G01N 2021/7786; G01N 21/77

See application file for complete search history.

(56) References Cited

U.S. PATENT DOCUMENTS

| | | | | |
|---|---|---|---|---|
| 9,943,845 | B2* | 4/2018 | Damit | B01L 3/5027 |
| 11,953,419 | B2* | 4/2024 | Hwang | B03C 3/53 |
| 2007/0059764 | A1* | 3/2007 | Hart | G01N 15/1459 |
| | | | | 435/7.1 |
| 2012/0174650 | A1* | 7/2012 | Ariessohn | B03C 3/41 |
| | | | | 73/23.2 |
| 2013/0217583 | A1* | 8/2013 | Link | C40B 30/04 |
| | | | | 506/9 |

FOREIGN PATENT DOCUMENTS

| | | | | |
|---|---|---|---|---|
| JP | 4797652 | B2 | 10/2011 | |
| JP | 5059740 | B2 | 10/2012 | |
| KR | 10-1568333 | B1 | 11/2015 | |
| KR | 10-2016-0111140 | A | 9/2016 | |
| KR | 20160145416 | A * | 12/2016 | B03C 3/017 |
| KR | 10-2017-0012260 | A | 2/2017 | |
| KR | 10-1912521 | B1 | 10/2018 | |
| KR | 10-2001770 | B1 | 7/2019 | |

OTHER PUBLICATIONS

Park, JW et al., "Continuous and real-time bioaerosol monitoring by combined aerosol-to-hydrosol sampling and ATP bioluminescence assay", Anal Chim Acta</i>, 2016; 941:pp. 101-107 (7 pages); doi: 10.1016/j.aca.2016.08.039. (Year: 2016).*
Park, JW et al., "Continuous and real-time bioaerosol monitoring by combined aerosol-to-hydrosol sampling and ATP bioluminescence assay", Anal Chim Acta</i>, </i>2016; 941:pp. 101-107 (7 pages); doi: 10.1016/j.aca.2016.08.039. (Year: 2016).*
Tseng, CC et al., "Optimization of a Portable Adenosine Triphosphate Bioluminescence Assay Coupled with a Receiver Operating Characteristic Model to Assess Bioaerosol Concentrations on Site", Microorganisms</i>, Jun. 29, 2020; 8(7):975, 19 pages; doi: 10.3390/microorganisms8070975. (Year: 2020).*
Park, JW et al., "Continuous and real-time bioaerosol monitoring by combined aerosol-to-hydrosol sampling and ATP bioluminescence assay", Anal Chim Acta, 2016; 941:pp. 101-107 (7 pages); doi: 10.1016/j.aca.2016.08.039. (Year: 2016).*
Translation of KR20160145416A—Description and Claims. Accessed on Jul. 1, 2024. Espacenet. https://worldwide.espacenet.com/patent/search?q=pn%3DKR20160145416A (Year: 2016).*

* cited by examiner

Primary Examiner — Aaron J Kosar
Assistant Examiner — Andrew T Moehlman

(57) ABSTRACT

Disclosed is an apparatus for monitoring bioaerosols, which includes a capturer configured to capture bioaerosol particles in air in a capture solution; a first droplet discharger configured to electro-spray the capture solution, in which the particles are captured, in a form of first droplets; a second droplet discharger configured to electro-spray a reagent, capable of reacting with the particles of the first droplets, in a form of second droplets; a reactor in which the first and second droplets are mixed so that the particles react with the reagent; and a measurer configured to measure the particles reacted with the reagent, wherein a size of the first droplets discharged from the first droplet discharger is controlled such that the particles are individually included in the first droplets. In accordance with such a configuration, individual particles can react with a reagent, which allows accurate bioaerosol monitoring optically.

3 Claims, 4 Drawing Sheets

[FIG. 1]
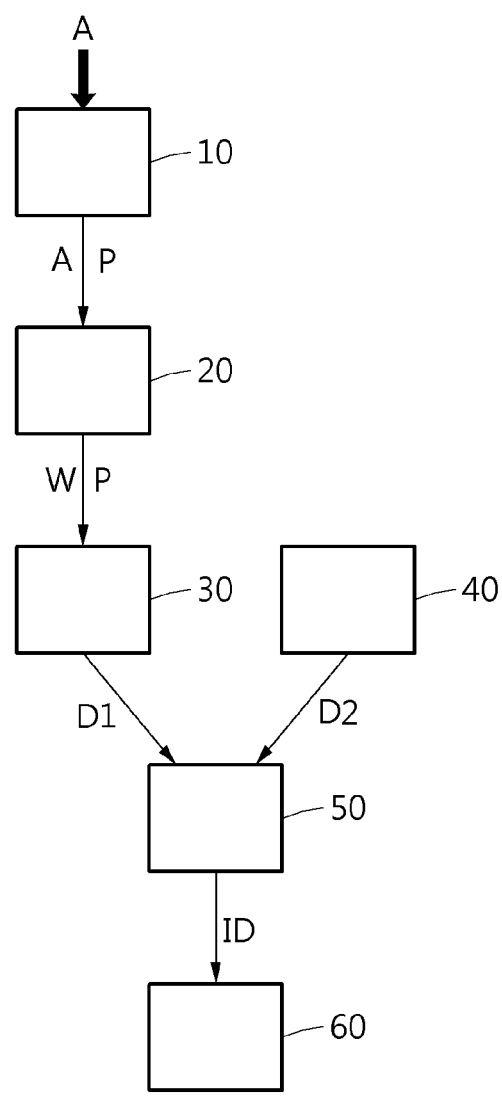

[FIG. 2]
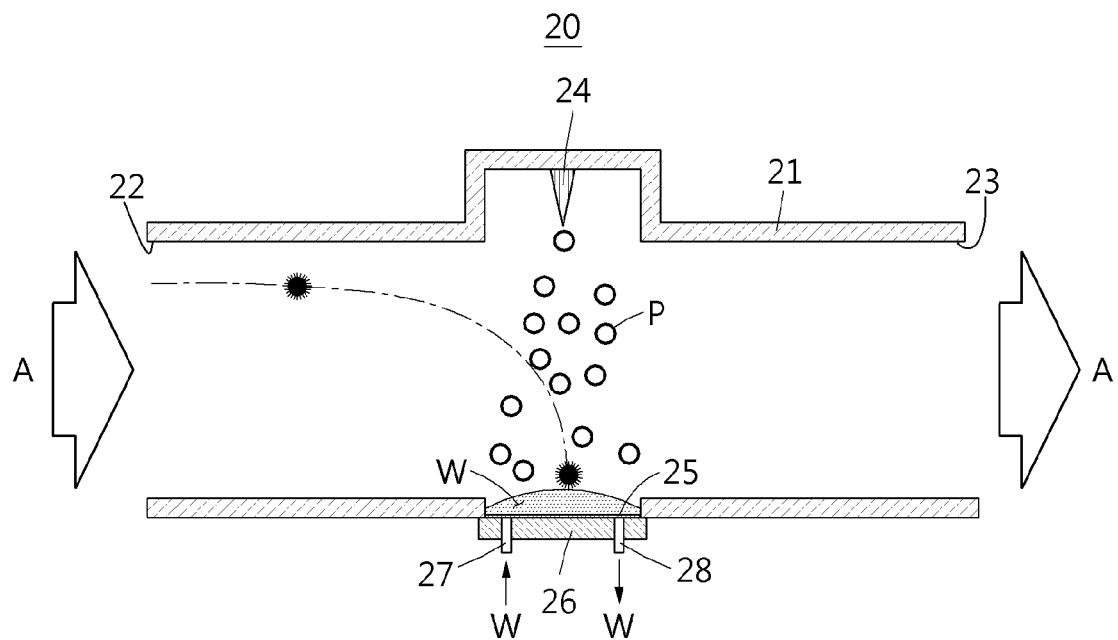

[FIG. 3]
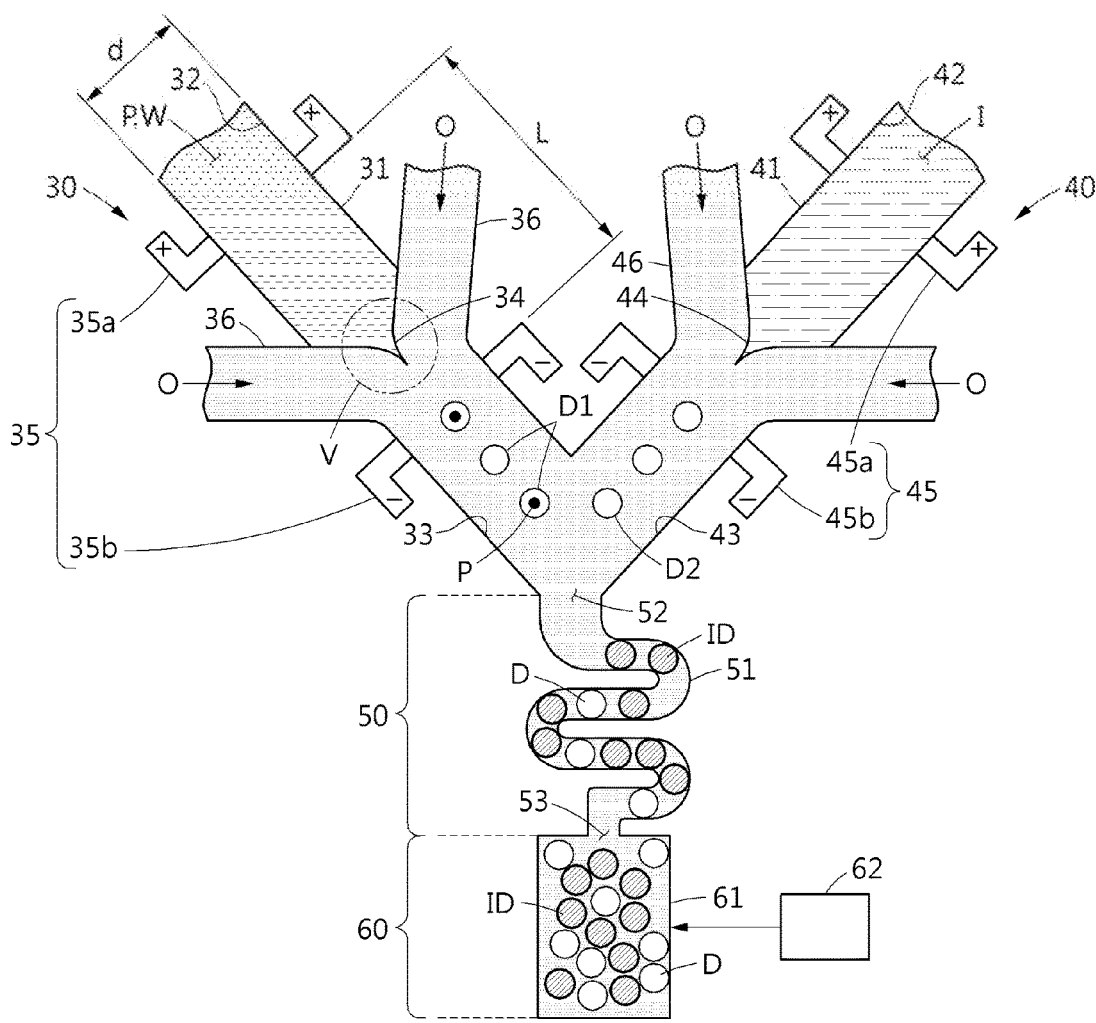

[FIG. 4]
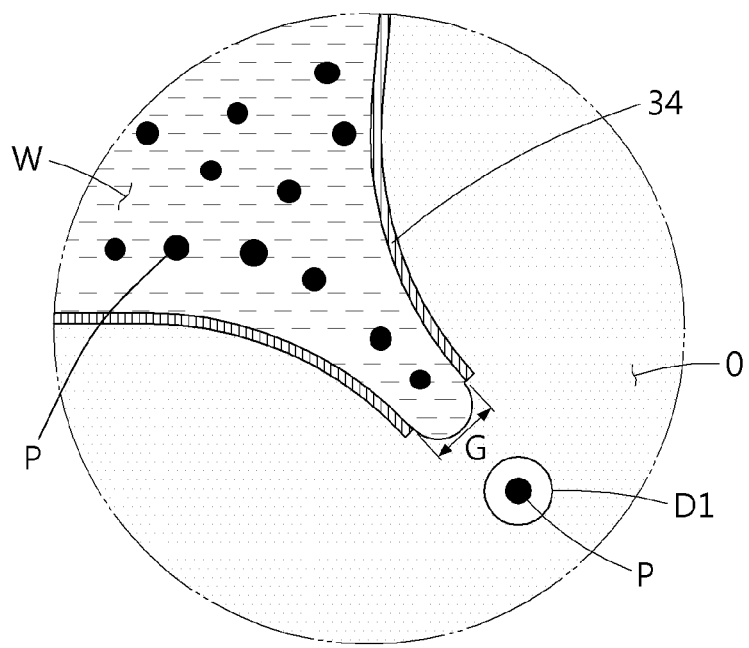

APPARATUS FOR MONITORING BIOAEROSOLS AND METHOD THEREOF

BACKGROUND OF THE DISCLOSURE

Field of the Disclosure

The present disclosure relates to an apparatus for monitoring bioaerosols and a method thereof, and more particularly, to an apparatus for monitoring bioaerosols configured to spray particles in air in the form of individual droplets in an electrostatic spray manner using a Taylor cone to be reacted with a reagent and thus enable accurate monitoring optically, and a method thereof.

Description of the Related Art

As general methods of measuring microorganisms, i.e., bioaerosols, suspended in air, a culture method of allowing biological particles suspended in a sample gas to be captured to a solid or liquid surface suitable for proliferation and culturing the same in an appropriate temperature and humidity environment for a certain period to measure the captured microorganisms; and a staining method of staining captured microorganisms and measuring the same using a fluorescence microscope are mainly used.

Recently, a series of processes required for ATP scavenging, ATP extraction, and light emission amount measurement can be shortened to about 30 minutes by an ATP bioluminescence method of using the principle that adenosine triphosphate (ATP) and luciferin/luciferase react to emit light, which allows rapid measurement.

Meanwhile, in the case of such a general bioaerosol measurement method, it is difficult to measure microorganisms floating in air in real time, and a high skill level of a measurer who can accurately perform each measurement step is required. In addition, since equipment for measuring microorganisms floating in air is very expensive, it is difficult for general users to use the same easily.

Accordingly, instead of existing limited bioaerosol measurement methods, various research that enables users to easily access in various places and make accurate measurements in real time is continuously being conducted in recent years.

RELATED ART DOCUMENTS

Patent Documents

Korean Patent No. 10-1912521
Japanese Patent No. 4797652

SUMMARY OF THE DISCLOSURE

Therefore, the present disclosure has been made in view of the above problems, and it is an object of the present disclosure to provide an apparatus for monitoring bioaerosols configured to individually electro-spray bioaerosol particles to react with a reagent, thereby enabling accurate bioaerosol monitoring optically.

It is another object of the present disclosure to provide a bioaerosol monitoring method of individually electro-spraying bioaerosol particles to react with a reagent, thereby being capable of improving measurement accuracy.

In accordance with an aspect of the present disclosure, the above and other objects can be accomplished by the provision of an apparatus for monitoring bioaerosols, the apparatus including: a capturer configured to capture bioaerosol particles in air in a capture solution; a first droplet discharger configured to electro-spray the capture solution, in which the particles are captured, in a form of first droplets; a second droplet discharger configured to electro-spray a reagent, capable of reacting with the particles of the first droplets, in a form of second droplets; a reactor in which the first and second droplets are mixed so that the particles react with the reagent; and a measurer configured to measure the particles reacted with the reagent, wherein a size of the first droplets discharged from the first droplet discharger is controlled such that the particles are individually included in the first droplets.

In addition, the apparatus may further include a classifier configured to aerodynamically classifying the microbial particles in air, wherein the particles are classified by the classifier and introduced into the capturer.

In addition, the first droplet discharger may include: a first discharge body provided with a particle inlet into which the capture solution capturing the particles are introduced; and a particle outlet configured to extend in a longitudinal direction from the particle inlet and discharge the first droplets to the reactor; a first discharge cone with a Taylor cone shape provided between the particle inlet and the particle outlet and configured to electro-spray the capture solution to be discharged in the form of the first droplets individually including the particles; a first controller configured to control such that an electrostatic force greater than surface tension of the capture solution is applied to the first discharge cone to control opening and closing of the first discharge cone; and a first oil supplier configured to supply an oil to the first droplets to maintain a state of the first droplets discharged through the first discharge cone.

In addition, the second droplet discharger may include: a second discharge body provided with a reagent inlet into which the reagent is introduced; and a reagent outlet configured to extend in a longitudinal direction from the reagent inlet and discharge the second droplets to the reactor; a second discharge cone with a Taylor cone shape provided between the reagent inlet and the reagent outlet and configured to individually electro-spray the second droplets; a second controller configured to control such that an electrostatic force greater than surface tension of the reagent is applied to the second discharge cone to control opening and closing of the second discharge cone; and a second oil supplier configured to supply an oil to the second droplets to individually maintain a state of the second droplets discharged through the second discharge cone.

In addition, the first controller may control the first discharge cone to be opened to a size of less than 1 μm such that the particles having a size of less than 1 μm are individually included in the first droplets.

In addition, the capture solution, in which the particles are captured, and the oil may be supplied in a flow rate ratio of 5 μL/hour:400 μL/hour to the first discharge body, the first discharge cone is disposed between a first positive electrode application body and a first negative electrode application body for respectively applying a positive electrode and a negative electrode, and a voltage of 5500 to 6500 V is applied to the first positive electrode application body and the first negative electrode application body, and the oil includes 3 to 7% of a surfactant.

In addition, an opening size of the second discharge cone may be controlled to less than 1 μm by the second controller.

In addition, the reactor may be provided with a reaction path bent a plurality of times such that the first and second droplets are mixed in the reaction path.

In addition, the reagent may include a fluorescent liquid capable of reacting with microorganisms.

In addition, the reagent may react with the particles to stain the particles, and the measurer may measure the stained particles optically using a photosensor or a fluorescence microscope.

In accordance with another aspect of the present disclosure, there is provided an apparatus for monitoring bioaerosols, including: a first droplet discharger having a first Taylor cone configured to electro-spray first droplets that individually include particles captured in a capture solution; a second droplet discharger having a second Taylor cone configured to electro-spray a reagent, capable of reacting with the particles, in a form of second droplets to the first droplets; a reactor in which the first and second droplets are reacted; and a measurer configured to measure the particles reacted with the reagent.

In addition, the first droplet discharger may include: a first discharge body which is provided with the first Taylor cone and into which the capture solution is introduced; a first controller configured to apply voltage to a positive electrode application body and a negative electrode application body between which the first Taylor cone is disposed, so as to generate an electrostatic force greater than surface tension of the capture solution and thus control opening and closing of the first Taylor cone; and a first oil supplier configured to supply an oil to the first droplets discharged from the first Taylor cone, and the second droplet discharger may include: a second discharge body which is provided with the second Taylor cone and into which the reagent is introduced; a second controller configured to apply voltage to a positive electrode application body and a negative electrode application body between which the second Taylor cone is disposed, so as to generate an electrostatic force greater than surface tension of the reagent and thus control opening and closing of the second Taylor cone; and a second oil supplier configured to supply an oil to the second droplets discharged from the second Taylor cone.

In addition, the first controller may control the first Taylor cone to be opened to a size of less than 1 μm such that the particles having a size of less than 1 μm are individually included in the first droplets.

In addition, the capture solution, in which the particles are captured, and the oil may be supplied in a flow rate ratio of 5 μL/hour:400 μL/hour to the first discharge body, the first Taylor cone is disposed between a first positive electrode application body and a first negative electrode application body for respectively applying a positive electrode and a negative electrode, and a voltage of 5500 to 6500 V is applied to the first positive electrode application body and the first negative electrode application body, and the oil includes 3 to 7% of a surfactant.

In addition, the reactor may be provided with a reaction path bent a plurality of times in which the first and second droplets are mixed and the particles are stained by the reagent, and the measurer may measure the stained particles optically using a photosensor or a fluorescence microscope.

In accordance with yet another aspect of the present disclosure, there is provided a method of monitoring bioaerosols, the method including: a particle discharge process of electro-spraying first droplets individually including bioaerosol particles captured in a capture solution; a reagent discharge process of electro-spraying a reagent, capable of reacting with the particles, in a form of second droplets toward the first droplets; a reaction process of mixing and reacting the reagent with the particles; and a measurement process of measuring the particles reacted with the reagent.

In addition, the particles particle discharge process and the reagent discharge process may be simultaneously performed.

In addition, the method may further include, before the particle discharge process, a capture process of capturing the particles in air into the capture solution by at least one of electrostatic precipitation, an impinger and a wet cyclone.

In addition, the particle discharge process may include: an introduction process of introducing the capture solution, in which the particles are captured, into a first discharge body; an electro-spraying process of electro-spraying the first droplets individually including the particles through a first discharge cone with a Taylor cone shape provided inside the first discharge body; and a first oil supply process of supplying an oil to the first droplets, wherein an electrostatic force greater than surface tension of the capture solution is applied to the first discharge cone to spray the first droplets.

In addition, the first discharge cone may be controlled to be opened to a size of less than 1 μm such that the particles having a size of less than 1 μm are individually included in the first droplets.

In addition, the reagent discharge process may include: an introduction process of introducing the reagent into a second discharge body; an electro-spray process of electro-spraying the second droplets from a second discharge cone with a Taylor cone shape provided inside the second discharge body; and a second oil supply process of supplying an oil to the second droplets, wherein an electrostatic force greater than surface tension of the reagent is applied to the second discharge cone to spray the second droplets.

In addition, in the reaction process, the particles may be stained by the reagent, and, in the measurement process, the particles stained by the reagent may be measured by means of a photosensor or a fluorescence microscope.

BRIEF DESCRIPTION OF THE DRAWINGS

The above and other objects, features and other advantages of the present disclosure will be more clearly understood from the following detailed description taken in conjunction with the accompanying drawings, in which:

FIG. 1 is a block diagram schematically illustrating an apparatus for monitoring bioaerosols according to a preferred embodiment of the present disclosure;

FIG. 2 is a block diagram schematically illustrating an embodiment of a capturer shown in FIG. 1;

FIG. 3 is a block diagram schematically illustrating a first droplet discharger, a second droplet discharger, a reactor and a measurer shown in FIG. 1; and FIG. 4 is a schematically enlarged view of a V region of FIG. 3.

DETAILED DESCRIPTION OF THE DISCLOSURE

Hereinafter, a preferred embodiment of the present disclosure is described with reference to the accompanying drawings. However, it should be understood that the spirit and scope of the present disclosure are not limited to the embodiments and can be modified by addition, modification, or deletion of elements constituting the embodiments and such additions, modifications, and deletions are also within the spirit and scope of the present disclosure.

Referring to FIG. 1, an apparatus 1 for monitoring bioaerosols according to a preferred embodiment of the present disclosure includes a classifier 10, a capturer 20, a first droplet discharger 30, a second droplet discharger 40, a reactor 50 and a measurer 60.

The classifier 10 serves to aerodynamically classify the microbial particles P in air A. The classifier 10 may include a virtual impactor provided with microchannels to classify, by size, the particles P in the introduced air A. Since the particle P classification technology of the classifier 10 including such a virtual impactor is not the gist of the present disclosure, detailed illustration and description thereof are omitted. In addition, a modified embodiment wherein the classifier 10 is not provided and the microbial particles P in air A are directly captured by the capturer 20 is also possible.

The capturer 20 captures the particles P floating in air A. In the present embodiment, it is exemplified that the particles P having a relatively small size, such as bacteria and viruses, among the microbial particles (P) in air A are captured. For reference, it is exemplified in the present disclosure that the particles P classified by size through the classifier 10 are introduced into the capturer 20, but the present disclosure is not necessarily limited thereto. That is, a modified embodiment wherein the particles P in air A are introduced into the capturer 20 without passing through the classifier 10 and without classification by size is also possible.

As shown in FIG. 2, by the capturer 20, the bioaerosol particles P included in air A are captured in the capture solution W. For this, the capturer 20 includes an inlet 22 into which the air A is introduced; and a capture tube 21 formed to penetrate between the inlet 22 and an outlet 23 extending in a longitudinal direction from the inlet 22 to face the inlet 22. In addition, it is exemplified that the capturer 20 includes first and second electrodes 24 and 25 disposed between the inlet 22 and outlet 23 of the capture tube 21 to face each other such that voltage can be applied to the first and second electrodes 24 and 25 and thus the particles P are captured in the capture solution W by electrostatic precipitation. Here, the first electrode 24 has a tip, and the second electrode 25 facing the first electrode 24 has a plate shape, but the present disclosure is not limited thereto.

The particles P in air A introduced into the inlet 22 of the capture tube 21 are captured in the capture solution W provided on the second electrode 25 side by electrostatic precipitation force generated between the first and second electrodes 24 and 25. Here, the capture solution W is introduced through a capture solution inlet 27 formed at the capture solution support 26, and then discharged through a capture solution outlet 28 formed thereat. For reference, it is exemplified that the capture solution W includes pure water (DI-Water) and the aerosol particles P including bacteria are captured in the capture solution W.

Meanwhile, the method of capturing the particles P, which are present in air A containing microorganisms such as bacteria, in the capture solution W is not limited to electrostatic precipitation as shown in FIG. 2, and any one of various methods of capturing the particles P in air A into the liquid capture solution W may be used. For example, it is natural that the capturer 10 may be modified to adopt various capture manners such as an impinger and a wet cyclone.

The first droplet discharger 30 electro-sprays the particles P captured in the capture solution W to individually discharge the particles P in the form of the first droplets D1. The first droplet discharger 30 includes a first discharge body 31, a first discharge cone 34, a first controller 35 and a first oil supplier 36, as shown in FIG. 3.

The first discharge body 31 is provided with a particle inlet 32 into which the particles P captured in the capture solution by the capturer 20 are introduced; and a particle outlet 33 configured to extend in a longitudinal direction from the particle inlet 32 and discharge the particles P to the reactor 50. The particles P captured in the capture solution W are introduced into the particle discharge body 31.

The first discharge cone 34 is provided between the particle inlet 32 and the particle outlet 33 and has a Taylor cone shape to discharge the particles P captured in the capture solution W through the particle inlet 32 in the form of the individual first droplets D1. The cone-shaped end of the first discharge cone 34 is a kind of nozzle, and is opened, as shown in FIG. 4, when an electrostatic force overcoming the surface tension is applied to electro-spray the particles P captured in the capture solution W in the form of the first droplets D1. Here, the size of the first droplets D1 to be electro-sprayed from the first discharge cone 34 may be adjusted by controlling an open area G of the particle discharge cone 24.

The first controller 35 controls an electrostatic force applied to the first discharge cone 34 to control opening and closing of the first discharge cone 34. The first controller 35 includes a first positive electrode application body 35*a* for applying a voltage to a positive electrode and a first negative electrode application body 35*b* for applying a voltage to a negative electrode. The first positive and negative electrode application bodies 35*a* and 35*b* are provided on the first discharge body 31, and the first discharge cone 34 is provided between the first positive and negative electrode application bodies 35*a* and 35*b*. A voltage to be applied to first positive and negative electrode application bodies 35*a* and 35*b* is controlled by the first controller 35. Accordingly, when electrostatic force generated by the first controller 35 is controlled to greater than the surface tension of the capture solution W in which the particles P are captured, the cone-shaped end of the first discharge cone 34 is opened and the particles P captured in the capture solution W are electro-sprayed in the form of the first droplets D1.

Here, the open area G of the end of the first discharge cone 34 may be controlled by adjusting an electrostatic force applied to the first controller 35 as shown in FIG. 4, so that the size of the first droplets D1 electro-sprayed from the first discharge cone 34 may be controlled. In addition, the first controller 35 may control an inclination angle formed by the first discharge cone 34, thereby controlling the size of the first droplets D1 to be sprayed from the particle discharge cone 34.

More particularly, when the open area G of the first discharge cone 34 is controlled to be opened to less than 1 μm by the first controller 35, the particles P having a size of less than 1 μm are sprayed in the form of the first droplets D1 through the first discharge cone 34. Here, since each of the first droplets D1 having a size of less than 1 μm discharged from the first discharge cone 34 may contain only one particle P such as bacteria having a size of about 0.6 to 0.8 μm, each of the first droplets D1 electro-sprayed through the first discharge cone 34 may contain only one particle P.

That is, since the size of the first droplets D1 sprayed through the first discharge cone 34 is 1 μm, microbial particles having a size of 1 μm or more may be contained in the first droplets D1, and the bioaerosol particles P, such as bacteria, having a size of less than 1 μm may be only sprayed in the form of the first droplets D1 together with the capture solution W. Here, the first droplets D1 discharged through the first discharge cone 34 may not include the particles P. That is, the first droplets D1 that have passed through the first discharge cone 34 may not contain the microbial particles P and may be discharged in the form of pure water (DI water), i.e., the capture solution W.

The first oil supplier 36 supplies the oil O to maintain the state of the first droplets D1 discharged through the first discharge cone 34. That is, the first oil supplier 36 supplies the oil O such that the shape of the first droplets D1 of the capture solution W wherein water is contained in the oil O is maintained like an emulsion wherein one of two liquids that do not dissolve each other is dispersed in the form of small particles on the other. The first oil supplier 36 supplies the oil O toward the end of the first discharge cone 34 such that the oil O is directly supplied to the first droplets D1 sprayed from the first discharge cone 34.

In the present embodiment, it is exemplified that a pair of first oil supplier 26 are provided to face each other toward the end of the first discharge cone 34 so as to supply the oil O, but the present disclosure is not necessarily limited thereto.

Meanwhile, it is exemplified that the first positive and negative electrode application bodies 35*a* and 35*b* of the first droplet discharger 30 described in the present embodiment include an ITO electrode, and a spacing L between the first positive and negative electrode application bodies 35*a* and 35*b* is about 4 mm. In addition, it is exemplified that the diameter d of the particle inlet 32 is about 0.1 mm.

In addition, an application voltage required to discharge the first droplets D1 through the first discharge cone 34 may be about 4000 V, and the following conditions may be applied to adjust the size of the first droplets D1 to 1 μm. That is, the capture solution W, in which the particles P introduced into the particle inlet 32 are captured, and the oil O may be supplied to the particle discharge body 31 in a ratio of a flow rate of the capture solution W:a flow rate of the oil O of 5 μL/hour:400 μL/hour, a voltage applied to the first positive and the negative electrode application bodies 35*a* and 35*b* may be about 6000 V, and the concentration of a surfactant such as Span 80 that may be contained in the oil O may be about 3 to 7%. Under such conditions, the first discharge cone 34 may discharge the first droplets D1 having a size of 1 μm.

The second droplet discharger 40 electro-sprays a reagent I, capable of reacting with the particles P, toward the first droplets D1 sprayed from the first droplet discharger 30. The first droplet discharger 30 includes a second discharge body 41, a second discharge cone 44, a second controller 45 and a second oil supplier 46, similar to the first droplet discharger 30 described above.

For reference, it is exemplified that the reagent I described in the present disclosure includes a fluorescent liquid including luciferin/luciferase capable of fluorescently reacting to microorganisms in an ATP manner, but the present disclosure is not necessarily limited thereto.

The second discharge body 41 is provided with a reagent inlet 42 into which the reagent I is introduced; and a reagent outlet 43 configured to extend in a longitudinal direction from the reagent inlet 42 to discharge the reagent I into the reactor 50. Here, the reagent outlet 43 of the second discharge body 41 communicates with the particle outlet 33 of the first discharge body 31, and the particle outlet 33 and the reagent outlet 43, which communicate with each other, of the first and second discharge bodies 31 and 41 are connected to the reactor 50. Accordingly, the particle outlet 33 and the reagent outlet 43 have a “Y” shape separated by two prongs with respect to the reactor 50.

The second discharge cone 44 is provided between the reagent inlet 42 and the reagent outlet 43 and has a Taylor cone shape to electro-spray the reagent I introduced through the reagent inlet 42 so as to discharge in the form of second droplets D2 containing the reagent I.

The reagent controller 35 controls opening and closing of the second discharge cone 44 so as to control spray of the second droplets D2 containing the reagent I discharged through the second discharge cone 44. That is, the second controller 45 includes the second positive and negative electrode application bodies 45*a* and 45*b* to apply an electrostatic force greater than the surface tension of the reagent I, similar to the aforementioned first controller 35. The second positive and negative electrode application bodies 45*a* and 45*b* are provided on the second discharge body 41, and the second discharge cone 44 is provided between the second positive and negative electrode application bodies 45*a* and 45*b*. The second positive and negative electrode application bodies 35*a* and 35*b* control electrostatic force generated by voltage application to be greater or smaller than the surface tension of the reagent I to open or close the second discharge cone 44.

Here, the second controller 45 controls the second discharge cone 44 to be opened to a size of less than 1 μm so as to electro-spray the reagent I in the form of the second droplets D2, similar to the first controller 35. However, the present disclosure is not necessarily limited thereto, and it is natural that the opening area and conditions of the second discharge cone 44 may be variously changed.

The second oil supplier 46 supplies the oil O to maintain the state of the second droplets D2 discharged through the second discharge cone 44. The second supplier 46 supplies the oil O toward the end of the second discharge cone 44 to directly supply the oil O to the second droplets D2 sprayed from the second discharge cone 44, similar to the first oil supplier 36. In addition, it is illustrated and exemplified that a pair of second oil suppliers 46 are provided to face each other toward the end of the second discharge cone 44 so as to supply the oil O, but the present disclosure is not necessarily limited thereto.

For reference, when the second droplet discharger 40 is controlled in the same manner as in the first droplet discharger 30 described above, the second discharge cone 44 may easily charge the second droplets D2 having a size of about 1 μm.

The particles P contained in the first droplets D1 and the reagent I in the second droplets D2, which are individually electro-sprayed through the first droplet discharger 30 and the second droplet discharger 40, are mixed and reacted in the reactor 50. The reactor 50 includes the reaction path 51 bent a plurality of times, as shown in FIG. 3. Here, the first and second droplets D1 and D2 are introduced into the reaction path 51 through a mixing inlet 52 and mixed and reacted with each other via the reaction path 51, followed by being discharged through a mixing outlet 53.

For reference, the particles P among the first droplets D1 react with the second droplets D2 including the reagent I via the reaction path 51 to be stained in a state of reacted droplets ID. In addition, the first droplets D1 excluding the particles P do not react with the second droplets D2, thereby maintaining the state of the first droplets D1.

The measurer 60 measures the particles P reacted with the reagent I. That is, the measurer 60 measures the reacted droplets ID which are mixtures of the particle P-containing first droplets D1, among the first droplets D1 sprayed from the particle sprayer 20, and the reagent I-containing second droplets D2 mixed and stained in the reactor 50. The measurer 60 includes a collection container 61 in which the reacted droplets ID and the first droplets D1 discharged from the reactor 50 are collected; and a detection means 62 for measuring the reacted droplets ID collected in the collection container 61, as shown in FIG. 3.

The collection container 61 communicates with a mixing outlet 53 of the reactor 50. In the collection container 61, the reacted droplets ID reacted with the reagent I to be stained; and the first droplets D1 excluding the particles P and thus unreacted with the reagent I are collected. In addition, the oil O discharged from the first and second oil suppliers 36 and 46 and provided to maintain a droplet shape is also collected in the collection container 61.

It is exemplified that the detection means 62 includes at least one of equipment, such as a photosensor or a fluorescence microscope, for detection of the reacted droplets ID optically. In the present embodiment, it is exemplified that the reagent I includes luciferin/luciferase and, accordingly, the detection means 62 is a fluorescence microscope capable of photographing the particles P that fluorescently react with the reagent I.

A method of monitoring bioaerosols using the apparatus 1 for monitoring bioaerosols according to the present disclosure having the above configuration is described with reference to FIGS. 1 to 4.

The method of monitoring bioaerosols includes a capture step, a particle discharge step, a reagent discharge step, a reaction step and a measurement step.

In the capture step, the bioaerosol particles P, such as bacteria, in air A are captured in the capture solution W. In the capture step, the particles P are aerodynamically separated using the classifier 10, and then the particles P are captured in the capture solution W as shown in FIG. 2.

In the particle discharge step, the particles P captured in the capture solution W are individually electro-sprayed in the form of the first droplets D1. In such a particle discharge step, the capture solution W including the particles P introduced into the first discharge body 31 is electro-sprayed in the form of the first droplets D1 from the first discharge cone 34 having a Taylor cone shape, as shown in FIGS. 3 and 4. Here, an electrostatic force applied to the first discharge cone 34 is controlled by the first controller 35, and the first droplets D1 are introduced to the reactor 50 side while maintaining the droplet shape thereof due to the oil O that is supplied from the first oil supplier 36 as soon as the first droplets D1 are discharged.

In the reagent discharge step, the reagent I is electro-sprayed in the form of droplets, similar to the shape of the second droplets D2, by controlling an electrostatic force, applied to the second discharge cone 44 with a Taylor cone shape, by the second controller 45, as shown in FIG. 3. Here, the second droplets D2 are introduced the reactor 40 while maintaining the droplet shape thereof due to the oil O supplied from the second oil supplier 46 as soon as the second droplets D2 are discharged.

For reference, the particle discharge step and the reagent discharge step are preferably performed at the same time so that the second droplets D2 are introduced into the reactor 50 while maintaining the droplet shape thereof due to the oil O. However, the present disclosure is not necessarily limited thereto, and the reagent discharge step may be performed after the particle discharge step or the first droplets D1 may be electro-sprayed in the particle discharge step after previously electro-spraying the second droplets D2 containing the reagent I in the reagent discharge step.

In the reaction step, the first and second droplets D1 and D2 are introduced into the reaction path 51 bent a plurality of times and mixed and reacted while passing through the reaction path 51, as shown in FIG. 3. Here, the particle P-containing first droplets D1 among the first droplets D1 react with the reagent I of the second droplets D2 to be stained in the form of the reacted droplets ID, and the first droplets D1 excluding the particles P only contain the capture solution W as a pure component and thus do not react with the second droplets D2, thereby maintaining the state of the first droplets D1.

In the measurement step, the reacted droplets ID that have been subjected to the reaction step are collected in the collection container 61 of the measurer 60, and then measured by means of the detection means 62 such as a photosensor or an optical microscope. Accordingly, finally, the distribution, number, volume, etc. of the bioaerosol particles P of included in air A are finally detected and monitored in real time.

In accordance with the present disclosure having the above configuration, first, particles such as bacteria floating in air are individually electro-sprayed and reacted with a reagent, which allows accurate bioaerosol measurement optically.

Second, accurate bioaerosol measurement can be performed, and thus, bioaerosols can be monitored in real time.

Third, an apparatus for measuring bioaerosols according to the present disclosure has a simple structure, which is advantageous in reducing manufacturing costs.

While the present disclosure has been described referring to the preferred embodiments, those skilled in the art will appreciate that many modifications and changes can be made to the present disclosure without departing from the spirit and essential characteristics of the present disclosure.

| [Description of Symbols] | |
| --- | --- |
| 1: apparatus for monitoring bioaerosols | 10: classifier |
| 20: capturer | 30: first droplet discharger |
| 31: first discharge body | 34: first discharge cone |
| 35: first controller | 36: first oil supplier |
| 40: second droplet discharger | 41: second discharge body |
| 44: second discharge cone | 45: second controller |
| 46: second controller | 50: reactor |
| 51: reaction path | 60: measurer |
| P: particle | D1: first droplet |
| D2: second droplet | ID: reacted droplet |

What is claimed is:

1. An apparatus for monitoring bioaerosols, comprising:
a capturer configured to capture bioaerosol particles in air in a capture solution,
wherein the capturer comprises:
an inlet into which the air is introduced,
a capture tube formed to penetrate between the inlet and an outlet extending in a longitudinal direction from the inlet to face the inlet,
a first electrode having a tip shape and a second electrode having a plate shape, wherein the first electrode and the second electrode are disposed in the capture tube and facing each other, and the capture solution is provided on the second electrode through a capture solution inlet formed in a capture solution support and is discharged through a capture solution outlet formed in the capture solution support;
a first droplet discharger having a first Taylor cone configured to electro-spray first droplets that individually comprise particles captured in the capture solution;
a second droplet discharger having a second Taylor cone configured to electro-spray a reagent, capable of reacting with the particles, in a form of second droplets to the first droplets;
a reactor in which the first and second droplets are reacted; and a measurer configured to measure the particles reacted with the reagent, wherein the first droplet discharger comprises:

a first discharge body which is provided with the first Taylor cone and into which the capture solution capturing the particles is introduced;

a first controller configured to control voltage applied to a first positive electrode application body and a first negative electrode application body between which the first Taylor cone is disposed, to generate an electrostatic force greater than surface tension of the capture solution capturing the particles, and to control opening and closing of the first Taylor cone; and a pair of first oil suppliers provided to face each other toward the end of the first Taylor cone and configured to supply an oil to the first droplets discharged from the first Taylor cone, wherein the first controller controls the first Taylor cone to be opened to a size of less than 1 μm such that the particles having a size of less than 1 μm are individually comprised in the first droplets, wherein the capture solution capturing the particles and the oil are supplied in a flow rate ratio of 5 μL/hour:400 μL/hour to the first discharge body to adjust a size of the first droplets to 1 μm, wherein the second droplet discharger comprises:

a second discharge body which is provided with the second Taylor cone and into which the reagent is introduced;

a second controller configured to control voltage applied to a second positive electrode application body and a second negative electrode application body between which the second Taylor cone is disposed, to generate an electrostatic force greater than surface tension of the reagent, and to control opening and closing of the second Taylor cone; and a pair of second oil suppliers provides to face each other toward the end of the second Taylor cone and configured to supply an oil to the second droplets discharged from the second Taylor cone, wherein the second controller controls the second Taylor cone to be opened to a size of less than 1 μm to electro-spray the reagent in the form of the second droplets having a size of about 1 μm.

2. The apparatus according to claim 1, wherein the first Taylor cone is disposed between the first positive electrode application body and the first negative electrode application body for respectively applying a positive electrode and a negative electrode, and a voltage of 5500 to 6500 V is applied to the first positive electrode application body and the first negative electrode application body, and the oil comprises 3 to 7% of a surfactant to discharge the first droplets having the size of 1 μm, wherein the first positive electrode application body and the first negative electrode application body include an ITO electrode, a spacing between the first positive electrode application body and the first negative electrode application body is about 4 mm, and a diameter of a particle inlet is about 0.1 mm.

3. The apparatus according to claim 1, wherein the reactor includes a reaction path bent a plurality of times in which the first and second droplets are mixed and the particles are stained by the reagent in a state of reacted droplets, and the measurer measures the stained particles using a photosensor or a fluorescence microscope.

* * * * *